United States Patent
Blackwell

(10) Patent No.: US 8,507,570 B2
(45) Date of Patent: Aug. 13, 2013

(54) RADICAL POLYMERIZATION INHIBITORS FOR LIGHT-CURABLE DENTAL MATERIALS

(75) Inventor: Gordan Blackwell, Constance (DE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/344,873

(22) Filed: Jan. 6, 2012

(65) Prior Publication Data

US 2012/0142804 A1    Jun. 7, 2012

Related U.S. Application Data

(63) Continuation of application No. 12/941,518, filed on Nov. 8, 2010, now abandoned.

(51) Int. Cl.
| | |
|---|---|
| C08F 2/50 | (2006.01) |
| C08F 2/48 | (2006.01) |
| C08B 37/00 | (2006.01) |
| G03F 7/031 | (2006.01) |
| C08G 59/68 | (2006.01) |
| C08G 61/04 | (2006.01) |
| C04B 35/571 | (2006.01) |
| B29C 71/04 | (2006.01) |
| H05B 6/68 | (2006.01) |

(52) U.S. Cl.
USPC .......... 522/16; 522/12; 522/7; 522/8; 522/68; 522/13; 522/21; 522/22; 522/6; 522/71; 522/1; 520/1

(58) Field of Classification Search
USPC .............. 522/16, 12, 7, 8, 13, 21, 22, 6, 71, 522/1, 68; 520/1
See application file for complete search history.

(56) References Cited

U.S. PATENT DOCUMENTS

| | | | |
|---|---|---|---|
| 3,655,605 A | 4/1972 | Smith et al. | |
| 3,784,557 A | 1/1974 | Cescon | |
| 3,814,717 A | 6/1974 | Wilson et al. | |
| 4,143,018 A | 3/1979 | Crisp et al. | |
| 4,192,795 A * | 3/1980 | Madhavan et al. | 523/116 |
| 4,209,434 A | 6/1980 | Wilson et al. | |
| 4,360,605 A | 11/1982 | Schmitt et al. | |
| 4,376,835 A | 3/1983 | Schmitt et al. | |
| 6,174,935 B1 | 1/2001 | Matsunae et al. | |
| 2006/0280649 A1 * | 12/2006 | Grundler | 422/50 |

FOREIGN PATENT DOCUMENTS

| | | |
|---|---|---|
| EP | 0783881 A2 | 12/1996 |
| WO | 9740421 A1 | 10/1997 |
| WO | 0061073 A1 | 10/2000 |
| WO | 2006013111 A1 | 2/2006 |
| WO | 2006084769 A1 | 8/2006 |

OTHER PUBLICATIONS

E.Buelher, J. Org Chem, 1967, 32, 261.
R.F.Schoenewaldt, R.B. Kinnel, P. Davis, Org. Chem, 1968, 33, 4270.
I. Brunning, R. Grashey, H. Hauk, R. Huisgen, & H. Seidl, Org. Synth. 1966, 46, 127.
Organic Syntheses, Coll. vol. 5, 962 (1973); vol. 45, p. 96 (1965).
Wasson et al., New Aspects of the Setting of Glass-ionomer Cements, Journal of Dental Research; vol. 72, No. 2, Feb. 1993; pp. 481-483.

* cited by examiner

*Primary Examiner* — Ling Choi
*Assistant Examiner* — Jessica E Whiteley
(74) *Attorney, Agent, or Firm* — Leana Levin; Douglas J. Hura; David A. Zdurne

(57) ABSTRACT

A light-curable dental material is provided, comprising a polymerizable compound having at least one ethylenically unsaturated bond, a photopolymerization initiator for polymerizing said polymerizable compound, and a 1,3-dipolar compound as a polymerization inhibitor.

8 Claims, No Drawings

RADICAL POLYMERIZATION INHIBITORS FOR LIGHT-CURABLE DENTAL MATERIALS

This is a Continuation Application of U.S. application Ser. No. 12/941,518, filed Nov. 8, 2010 now abandoned.

FIELD OF THE INVENTION

The present invention relates to light-curable dental materials, such as dental composites, comprising at least one polymerizable compound, a photopolymerization initiator and a polymerzation inhibitor.

BACKGROUND TO THE INVENTION

Radical polymerisation of ethylenically unsaturated compounds is widely used to harden dental materials such as dental filling materials. In light-curable dental materials, the ethylenically unsaturated compounds are activated to be polymerisable by the application of light, since this allows a "command cure". By this means the ethylenically unsaturated substances remain workable for an indefinite time, but can be cured at will in a short time by the application of light. Generally the actinic light has a wavelength between about 200 nm and 700 nm, and more often between about 300 nm and 600 nm. In light-curable dental compositions, camphor quinone which allows photopolymerization with visible light is almost exclusively used in combination with an amine as a reductant (co-initiator).

In many cases, it is necessary or convenient to apply the activated dental material or to model it under ambient light. Very often a relatively strong ambient light is needed so that the modelling or application can be carried out with the necessary precision, which leads to several conflicts. If sufficient ambient light is present for accurate and precise use of the dental material, the life time of the activated material is reduced, and the time available for the modelling or application is also reduced. If less ambient light is present, the life time of the material and the time available to model it ("working time") is increased, but the precision of the modelling is reduced. The lifetime of the material towards ambient light may be increased by, for instance, reduction in the concentration of initiators, or increasing the amount of polymerisation inhibitor present. However both of these measures can lead to a decrease in the physical properties of the light-cured dental material.

It is therefore an object of the invention to provide a light-curable dental material having a sufficient working time under ambient light without compromising the physical properties of the cured dental material. It is another object of the invention to provide a further inhibitor for light-curable dental materials.

SUMMARY OF THE INVENTION

The invention provides a light-curable dental material comprising
  (a) a polymerizable compound having at least one ethylenically unsaturated bond
  (b) a photopolymerization initiator for polymerizing said polymerizable compound, and
  (c) a 1,3-dipolar compound.
The 1,3-dipolar compound may act as a polymerization inhibitor.

The invention further provides a light-cured dental material obtained or obtainable by light curing the light-curable dental materials of the invention. Further, a use of 1,3-dipolar compound in a light-curable dental material is provided, notably a use of a 1,3-dipolar compound as a photopolymerization inhibitor.

The invention further provides a light-curable surface coating, light-curable ink, or light-curable adhesive material comprising a polymerizable compound having at least one ethylenically unsaturated bond and a 1,3-dipolar compound as a polymerization inhibitor. Moreover, use of a 1,3-dipolar compound in a light-curable surface coating, light-curable ink, or light-curable adhesive material as a polymerization inhibitor.

In the present invention, it has surprisingly been found that the working time of light-curable materials can be extended if the 1,3-dipolar compounds described herein are added to light-curable materials, notably dental materials. Even more surprisingly, it has been found that the physical properties of the light-cured dental materials obtained from the light-curable dental materials do not deteriorate to a significant extent in spite of marked increase of the working time. 1,3-dipolar compounds have in common a delocalized electron system extending over at least 3 adjacent atoms. It is believed that this electron system can efficiently stabilize or trap one-electron oxidized and/or one-electron reduced radical states, whereby radicals occurring in the light-cured dental materials (e.g. due to ambient light) can be deactivated by the 1,3-dipolar compound, thereby preventing premature polymerization of the light-curable dental materials.

It is known that in radical polymerisation, a growing polymer chain may be terminated by combining the chain end radical with a second radical. This second radical may be derived from another growing polymer chain, or it may be derived from an added substance. Free radicals for inhibiting purposes are commonly derived from substances which are easily converted to a low energy radical under the prevailing conditions, or which provide easily extractable hydrogen atoms. Examples are the well known phenolic inhibitors known as BHT, BHA, etc. The inhibiting radical may also be present as a so called "free radical". For instance, it is described in EP 0783 881 that the 2,2-diphenyl-1-pricrylhydrazyl-radical galvinoxyl radical, triphenylmethyl radical, or 2,2,4,4-tetramethylpiperidinyl-1-oxy radical (TEMPO) may be used for the purpose of increasing the available working time of a light sensitive dental filling material. Although a prolonged working time under ambient light is provided by these compounds, each of them has certain disadvantages, for instance being highly coloured, highly reactive, oxidative, thermally unstable, or a combination of these. Conventional inhibitors can also be used to provide prolonged working times, but have the disadvantage that physical properties of the cured materials are impaired.

In the present invention it has been found that 1,3-dipolar compounds have a strong inhibiting effect but are nevertheless low in colour, as well as thermally and chemically stable. In contrast to the use of conventional inhibitors, physical properties of the cured materials are not impaired to a significant extent but may even be improved. Examples of such 1,3-dipolar compounds are sydnones, nitrilylides, nitrones, diazo compounds, azides, and carbonyl oxides. The term "1,3-dipolar compound" or "1,3-dipole" is used for those compounds in which a significant canonical form can be represented by a separation of charge over three atoms. This is illustrated below for the case of sydnones. The structure of a 1,3-dipolar compound can be written in the forms $-x^+-y-z^-$ where x, y, and z represent atoms, typically of the second row of the periodic table of elements, that may be the same or independently different, and the structure may be linear or part of a ring system. Any of x, y, and z may also carry independent substituents. Plus and minus charges are formal charges. Herein, the term "1,3-dipolar compound" includes salts of the 1,3-dipolar compound.

Examples of 1,3-dipolar compounds are shown in the structures below, where the groups R are for illustration purposes only and may independently be any suitable atom or group of atoms.

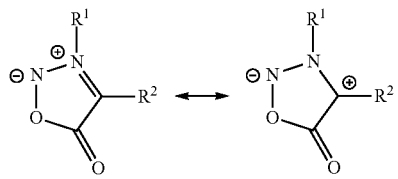

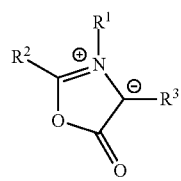

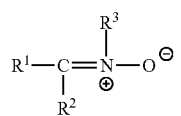

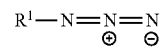

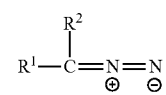

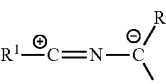

Formula (I) represents sydnones. Formula (II) represents munchnones. Formula (III) represents nitrones. Formula (IV) represents azides. Formula (V) represents diazo compounds. Formula (VI) represents nitrilylides (also referred to in the art as "nitrile ylides").

In the above formulae (I) to (VI), $R^1$, $R^2$, and $R^3$ may independently be hydrogen; or a substituted or unsubstituted aryl group, arylalkyl group, alkyl group, alkenyl group, alkynyl group, cycloalkyl group or cycloalkylalkyl group, except that $R^1$ of the compound of formula (IV) is not hydrogen. Hydrogen or a substituted or unsubstituted aryl or alkyl group are preferred.

In one embodiment, the 1,3-dipolar compound of the light-curable dental material is a sydnone of the following formula (VII).

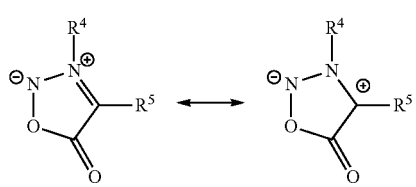

In formula (VII), $R^4$ and $R^5$ are independently hydrogen; or a substituted or unsubstituted aryl group, arylalkyl group, alkyl group, alkenyl group, alkynyl group, cycloalkyl group or cycloalkylalkyl group. Hydrogen or a substituted or unsubstituted $C_{1-6}$ alkyl or a substituted or unsubstituted $C_{6-14}$ aryl group, such as a substituted or unsubstituted $C_6$ or $C_{10}$ aryl group, are preferred.

In another embodiment, the 1,3-dipolar compound of the light-curable dental material is a nitrone of the following formula (VIII):

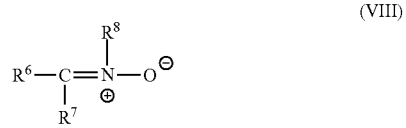

In the compound of formula (VIII), $R^6$, $R^7$, and $R^8$ may independently be the same as $R^4$ or $R^5$ defined above. Hydrogen or a substituted or unsubstituted $C_{1-6}$ alkyl or a substituted or unsubstituted $C_{6-14}$ aryl group, such as a substituted or unsubstituted $C_6$ or $C_{10}$ aryl group, are preferred. Further, $R^7$ and $R^8$ may form a 5-membered, 6-membered or 7-membered nitrogen-containing ring together with atoms to which they are attached to.

Examples of suitable nitrones include N-t-butyl-α-phenyl-nitrone, C,N-diphenyl-nitrone, C-phenyl-N-benzylnitrone, C-phenyl-N-ethylnitrone, C-phenyl-N-methylnitrone, and similar compounds, These nitrones can be prepared using the methods given for instance in E. Buelher, J. Org. Chem, 1967, 32, 261, E. F. Schoenewaldt, R-B. Kinnel, P. Davis, J. Org. Chem, 1968, 33, 4270, or I. Brüning, R. Grashey, H. Hauk, R. Huisgen, and H. Seidl, Org. Synth, 1966, 46, 127. Other methods of synthesis are also known and are described in the scientific literature.

In another embodiment, the 1,3-dipolar compound is a munchnone of the following formula (II):

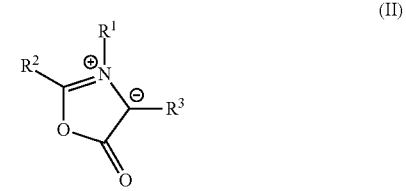

wherein $R^1$, $R^2$, and $R^3$ are independently as defined above for $R^4$ or $R^5$.

In another embodiment, the 1,3-dipolar compound is an azide of the following formula (IV):

wherein $R^1$ is a substituted or unsubstituted aryl group, arylalkyl group, alkyl group, alkenyl group, alkynyl group, cycloalkyl group or cycloalkylalkyl group, preferably a or substituted or unsubstituted $C_{1-6}$ alkyl group, or a substituted or unsubstituted $C_{6-14}$ aryl group. The stability of azides may be increased by using halogen or multiply halogen substituted aryl groups for $R^1$, such as chlorophenyl-, dichlorphenyl-, fluorophenyl-, pentafluorophenyl, chlorofluorophenyl.

In another embodiment, the 1,3-dipolar compound is a diazo compound of the following formula (V):

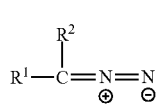

wherein $R^1$ and $R^2$ are independently as defined above for $R^4$ or $R^5$, preferably they are independently hydrogen, a substituted or unsubstituted $C_{1-6}$ alkyl group or a substituted or unsubstituted $C_{6-14}$ aryl or benzoyl group.

In another embodiment, the 1,3-dipolar compound is a nitrilylide of the following formula (VI):

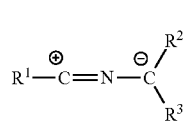

wherein each of $R^1$, $R^2$ and $R^3$ is, independently, as defined above for $R^4$ or $R^5$, preferably they are independently hydrogen, a substituted or unsubstituted $C_{1-6}$ alkyl group or a substituted or unsubstituted $C_{6-14}$ aryl group. In order to improve stability, at least one of $R^1$, $R^2$ and $R^3$ of the nitrilylide is preferably not hydrogen.

The substituted or unsubstituted alkyl group may be a substituted or unsubstituted $C_{1-6}$ alkyl group. The $C_{1-6}$-alkyl groups may by linear or branched $C_{1-6}$-alkyl groups. Examples of $C_{1-6}$ alkyl groups are methyl, ethyl, propyl (such as i-propyl or n-propyl), butyl (such as n-butyl, isobutyl, tert-butyl or sec-butyl), pentyl, and hexyl.

The substituted or unsubstituted alkenyl group may be a substituted or unsubstituted $C_{2-6}$ alkenyl group. Examples of the $C_{2-6}$ alkenyl group are ethenyl, propenyl, butenyl, pentenyl or hexenyl. The substituted or unsubstituted alkynyl group may be a substituted or unsubstituted $C_{2-6}$ alkynyl group. Examples of the $C_{2-6}$ alkynyl group are ethynyl, propynyl, propargyl, butynyl, pentynyl or hexynyl. The substituted or unsubstituted cycloalkyl group may be a $C_{3-6}$ cycloalkyl group. Examples of the $C_{3-6}$ cycloalkyl group are cyclopropyl, cyclobutyl, cyclopentyl or cyclohexyl.

The substituted or unsubstituted aryl group may be a substituted or unsubstituted $C_{6-14}$ aryl group such as a substituted or unsubstituted $C_6$ (i.e. phenyl) or $C_{10}$ (i.e. naphthyl) aryl group, a substituted or unsubstituted five-membered or six-membered heteroaromatic group or substituted or unsubstituted benzo-condensed analogs of five-membered or six-membered heteroaromatic groups. The heteroaromatic group may have from 1 to 3 heteroatoms selected from oxygen, nitrogen and sulfur. Examples of five-membered heteroaromatic groups are pyrrolyl, furyl, thienyl, pyrazolyl, imidazolyl, oxazolyl, isoxazolyl, thiazolyl, isothiazolyl, triazolyl. Examples of six-membered heteroaromatic groups are pyridyl, pyridazinyl, pyrimidinyl, pyrazinyl, thiazinyl, triazinyl. Examples of benzo-condensed analogs are indolyl, isoindolyl, quinolinyl, isoquinolinyl, quinazolinyl, quinoxalinyl, cinnolinyl, phthalazinyl, phenazinyl, phenoxazinyl, phenothiazinyl. A substituted or unsubstituted phenyl group is a preferred aryl group. Preferred substituted phenyl groups are halo substituted phenyl groups such as chlorophenyl, fluorophenyl, 2,4-dichlorophenyl, pentafluorophenyl.

The substituted or unsubstituted arylalkyl group may be a substituted or unsubstituted aryl-$C_{1-5}$ alkyl group, whereby the aryl group and the $C_{1-6}$ alkyl group may be as defined above. In the substituted arylalkyl group, the aryl and/or the alkyl moiety may be substituted as defined below.

The substituted or unsubstituted cycloalkylalkyl group may be a substituted or unsubstituted $C_{3-6}$-cycloalkyl-$C_{1-6}$-alkyl group, whereby the $C_{3-6}$-cycloalkyl group and the $C_{1-6}$-alkyl group may be as defined above.

The substituted or substituted aryl group, arylalkyl group, alkyl group, alkenyl group, alkynyl group, cycloalkyl group or cycloalkylalkyl group may have 1 to 5, preferably 1 to 3, substituents selected from $C_{1-6}$-alkyl, $C_{1-6}$-alkoxy, hydroxy, halo, cyano, nitro, nitroso, mercapto, carboxyl, sulfonate, thiol, amino, trifluoromethyl and polyoxyalkylene group, whereby $C_{1-6}$-alkyl, $C_{1-6}$-alkoxy, hydroxy, halo, cyano, nitro, nitroso, mercapto and trifluoromethyl are preferred.

In these substituents, the $C_{1-6}$-alkyl groups and the $C_{1-6}$-alkyl groups of the $C_{1-6}$-alkoxy groups may by linear or branched $C_{1-6}$-alkyl groups as defined above. "Halo" stands for the class consisting of fluoro, chloro, bromo and iodo.

The light-curable dental material of the invention contains a photopolymerization initiator for polymerizing said polymerizable compound. The photopolymerization initiator may be an α,β-diketone such as camphor quinone. Based on the total weight of all polymerizable compounds having at least one ethylenically unsaturated bond, the initiator (or the sum of all initiators if more than one is used) may be used in an amount of from 0.05 to 2.0, preferably from 0.1 to 1.3, and most preferably from 0.2 to 0.7 weight-%.

Preferably, the light-curable dental material comprises a photoinitiation system that comprises the photoinitiator(s) and a suitable co-initiator. The co-initiator may be selected from the following compound classes: thiols, heteroaromatic thiols, benzothiazoles, benzooxazoles, amines such as tertiary amines, alcohols, thiocarboxylic acids. Specific examples of co-initiators are dimethylamino benzoic acid ethyl ester, 4-dimethylaminobenzonitrile, 2-(4-dimethylaminophenyl) ethanol, dimethylethanolamine, dibutylethanolamine, 3-mercapto-4-methyl-4H-1,2,4-triazole or 2-mercapto-benzimidazole. The co-initiator may be used in an amount of from 0.01 to 2.0, preferably of from 0.05 to 1.5, more preferably of from 0.05 to 1.0, more preferably of from 0.1 to 1.0, and most preferably from 0.1 to 0.7 weight-% based on the total weight of all polymerizable compounds having at least one ethylenically unsaturated bond used in the light-curable dental material. It is possible to combine two or more different co-initiators in the light-curable dental material of the invention. In the latter case, the amounts given apply to the sum of all co-initiators used.

The wavelength range of the light used for light curing the material of the invention and the photoinitiator used are mutually adapted such that the light can activate the photoinitiator. A preferred photoinitiation system is the camphor quinone/amine system. Camphor quinone can be activated by blue visible light. A suitable light source is the Spectrum Lite™ from Dentsply. Alternatively, a hexarylbisimidazole/co-initiator system may be used. Further, it is possible to combine an α,β-diketone initiator such as camphor quinone and a hexarylbisimidazole in the light-curable dental material of the invention. Dyes may also be added in any of these systems as sensitizers to extend the absorption to longer wavelengths. A suitable light source for polymerising the light-curable dental materials of the invention is the Spectrum Lite™ from Dentsply.

The light-curable dental material of the invention may include a polymerization inhibitor other than the 1,3-dipolar compound. Examples of such polymerization inhibitors are phenolic compounds such as BHT or stable radicals such as 2,2,4,4-tetramethylpiperidinyl-1-oxy radical, 2,2-diphenyl-1-picrylhydrazyl radical, galvinoxyl radical, or triphenylmethyl radical. It is possible to combine two or more different polymerization inhibitors in the light-curable dental material of the invention. The amounts of the polymerization inhibitors is chosen such that a useful working time is achieved.

The light-curable dental material may be a dental composite material, a dental glass ionomer, a dental sealant, a dental adhesive, a adhesion promoter, an adhesion preventer, a cement, a crown-forming material, or an impression material. In an important embodiment, the light-curable dental material is a filler-containing light-curable dental material that contains at least 10 weight-% of a solid particulate filler. Depending on the type of the light-curable dental material, a suitable solvent may be present as generally known in the art.

The light-curable dental material of the invention contains at least one polymerizable compound having at least one ethylenically unsaturated bond. Said polymerizable compound having at least one ethylenically unsaturated bond may be a polymerizable(meth)acrylic monomer having a (meth)acryl moiety, or any other unsaturated bond polymerizable by radical polymerisation such as compounds comprising ally moieties, vinyl moieties, vinylcarboxyl moieties, (meth)acrylate ester moieties, or (meth)acrylate amide moieties.

In one embodiment, the light-curable dental material contains at least one polymerizable (meth)acrylic monomer having at least two polymerizable groups, such as at least two (meth)acrylic moieties, for allowing cross-linking upon light-curing. Said polymerizable (meth)acrylic monomer having at least two polymerizable groups has at least two (i.e. two, three, four or more) polymerizable groups. Such polymerizable monomers are known to the skilled person from conventional dental materials. Examples are di(meth)acrylates of alkanediols and other polyfunctional (meth)acrylates; urethane di(meth)acrylates which may be reaction products of 2 mol of a hydroxyalkyl(meth)acrylate with 1 mol of a diisocyanate. Specific examples include 1,3-butylene glycol di(meth)acrylate, 1,6-hexanediol di(meth)acrylate, neopentyl glycol di(meth)acrylate, bisphenol A di(meth)acrylate, bisphenol A glycidyl di(meth)acrylate, ethylene oxide-modified bisphenol A di(meth)acrylate, ethylene oxide-modified bisphenol A glycidyl di(meth)acrylate, 2,2-bis(4-methacryloxypropoxyphenyl)-propane, 7,7,9-trimethyl-4,13-dioxa-3,14-dioxo-5,12-diazahexadecane-1,1,6-diol di(meth)acrylate (UDMA), neopentyl glycol hydroxypivalate di(meth)acrylate, caprolactone-modified neopentyl glycol hydroxypivalate di(meth)acrylate, trimethylolethane di(meth)acrylate, trimethylolpropane di(meth)acrylate, and the like. 2, 3 or more different polymerizable monomers may be used as a mixture.

Examples of polymerizable (meth)acrylic monomers having three or more polymerizable groups are trimethylolmethane tri(meth)acrylate, trimethylolethane tri(meth)acrylate, trimethylolpropane tri(meth)acrylate, pentaerythritol tri(meth)acrylate, dipentaerythritol tri(meth)acrylate, pentaerythritol tetra(meth)acrylate, dipentaerythritol tetra(meth)acrylate, dipentaerythritol hexa(meth)acrylate, and the like.

Further examples of polymerizable compounds having at least one ethylenically unsaturated bond are polymerizable monomers like (meth)acrylic monomers having one (meth)acrylic moiety like methyl(meth)acrylate, ethyl(meth)acrylate, n-butyl(meth)acrylate, isobutyl(meth)acrylate, 2-ethylhexyl(meth)acrylate, lauryl(meth)acrylate, tridecyl(meth)acrylate, stearyl(meth)acrylate, cyclohexyl(meth)acrylate, benzyl(meth)acrylate, glycidyl(meth)acrylate, allyl(meth)acrylate, phenoxydiethylene glycol(meth)acrylate, phenoxyhexaethylene glycol(meth)acrylate, dicyclopentenyl(meth)acrylate, isobornyl(meth)acrylate, phenyl(meth)acrylate, caprolactone-modified tetrahydrofurfuryl(meth)acrylate, caprolactone-modified dipentaerythritol(meth)acrylate, (meth)acrylamide, ethylene-1,2-diamine di(meth)acrylamide, and caprolactone-modified 2-hydroxyethyl(meth)acrylate.

Examples of polymerizable compounds having at least one ethylenically unsaturated bond other than (meth)acrylic moieties are 1-alkenes, such as 1-hexene, 1-heptene; branched alkenes, such as vinylcyclohexane, 3,3-dimethyl-1-propene, 3-methyl-1-diisobutylene, 4-methyl-1-pentene; vinyl esters, such as vinyl acetate; styrene, substituted styrenes having an alkyl substituent in the side chain, e.g. alpha-methylstyrene, substituted styrenes having an alkyl substituent on the ring, such as vinyltoluene and p-methylstyrene, halogenated styrenes, such as monochlorostyrenes and dichlorostyrenes; or heterocyclic vinyl compounds, such as 2-vinylpyridine, 3-vinylpyridine, 2-methyl-5-vinylpyridine, 3-ethyl-4-vinylpyridine, 2,3-dimethyl-5-vinylpyridine, vinyl-pyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinyl-pyrrolidone, N-vinylpyrrolidine, 3-vinylpyrrolidine, N-vinylcaprolactam, N-vinylbutyrolactam, vinyloxolane, vinylfuran; vinyl and isoprenyl ethers; maleic acid derivatives, such as maleic anhydride, methylmaleic anhydride, maleimide, methylmaleimide; and dienes, such as divinylbenzene. The polymerizable compounds may be employed as a mixture. They may be used to adjust the mechanical properties of the polymerized light-cured dental material as the case requires.

In one embodiment; the light-curable dental material is a filler-containing light-curable dental material, such as a dental composite. In this embodiment, the light-curable dental material of the invention comprises a solid particulate filler and a polymerizable matrix, wherein the polymerizable matrix comprises (i) one or more polymerizable compounds each having at least one ethylenically unsaturated bond,
(ii) a photopolymerization initiator for polymerizing said polymerizable compounds, and
(iii) a 1,3-dipolar compound.

The light-curable dental composite of the invention contains a solid particulate filler that provides strength to the polymerized dental composite of the invention. The solid filler is a finely divided particulate material. The light-curable dental composite of the invention contains at least 10% by weight, preferably at least 20% by weight, more preferably at least 50% by weight, and most preferably at least 70% by weight of said solid filler based on the total weight of said light-curable dental composite. The filler content may be expressed as volume-%, which makes the numerical value of the filler content independent of the density of said solid filler. Using this definition, the dental composite of the invention contains generally at least 4% by volume, preferably at least 8% by volume, more preferably at least 25% by volume, even more preferred at least 35% by volume and most preferably at least 45% by volume of said solid filler. Obviously, the exact amount of said solid filler that can be incorporated into said polymerizable matrix depends on the size of the particles of said solid filler, i.e. on the surface area of said solid filler, and on the density of the filler.

Suitable fillers that may be used in the filler-containing light-curable dental material, notably the light-curable dental composite, include organic and inorganic solid fillers, whereby inorganic fillers are preferred. Examples of inorganic fillers are glasses e.g. those containing barium, strontium, boron, or zinc, aluminosilicate glass, and metal oxides such as zinc oxide, zirconium oxide, aluminium oxide, silica, apatite, or a cured mixture of resin and filler ground or otherwise reduced in size to a powder. Other examples are fused silica, quartz, crystalline silica, amorphous silica, soda glass beads, glass rods, ceramic oxides, particulate silicate glass, radiopaque glasses (barium and strontium glasses), and synthetic minerals. It is also possible to employ finely divided materials and powdered hydroxyl-apatite, although materials that react with silane coupling agents are preferred. Also available as a filler are colloidal or submicron silicas coated with a polymer. As further examples of suitable inorganic fillers may be mentioned $La_2O_3$, $ZrO_2$, $BiPO_4$, $CaWO_4$, $BaWO_4$, $SrF_2$, $Bi_2O_3$. Suitable organic fillers include polymer granulates such as polytetrafluoroethylene particles. Small amounts of pigments to allow matching of the composition to various shades of teeth can be included.

The particles of said solid filler should have a mean size below 100 μm, preferably below 50 μm, more preferably below 20 μm. Two or more solid fillers may be mixed that differ in their mean particle size. The particle size distribution may be monomodal or may be polymodal. Preferably, the particle size distribution is bimodal, e.g. as described in WO 2000/61073. The particles may be of any desired shape, for instance spherical, irregular as is obtained by mechanical particle size reduction, fibres, whiskers, platelets, dumbbell shaped, or cylindrical, and may be solid, hollow, or porous. Solid fillers that may be used in the present invention are known in the art. Inorganic fillers are preferably silanated before use in the present invention to render the surface of the filler particles more hydrophobic. Silanating agents for this purpose are well known in the art, e.g. 3-methacryloxypropyltrimethoxysilane.

The polymerizable matrix of the light-curable dental composite of the invention may further comprise from 1.0 to 50, preferably from 1.0 to 15 weight-% of at least one polymerizable monomer having a carboxylic acid group based on the total weight of said polymerizable matrix, said polymerizable monomer having a carboxylic acid group. Regarding said polymerizable monomer having a carboxylic acid group and the amounts of it to be used in the polymerizable matrix of the light-curable dental composite, reference is made to WO 2006/084769 that is included herein by reference in its entirety.

The light-curable dental composite typically further contains a suitable co-initiator or photopolymerization system as described above.

In another embodiment, the filler-containing light-curable dental material is a dental glass ionomer cement. Ionomer cements commonly contain a polycarboxylic acid and an inorganic powder which react in the presence of water by a curing reaction. Conventional ionomer cements generally contain a powder component containing aluminosilicate and a liquid portion usually containing a polyacid such as polyacrylic acid, polymaleic acid, polyitaconic acid, or a copolymer of at least two of the acids, cf. "New Aspects of the Setting of Glass-ionomer Cements," Wasson et al., Journal of Dental Research; Vol. 72, No. 2, February, 1993; pages 481-483. In glass ionomer cements, the primary reactions which cause the glass ionomer cement to harden is cross-linking of polycarboxylate chains by metal ions from the glass based on ionic forces. Moreover, during setting the acids of the glass ionomer cement dissolve the glass structure to release metal constituents of the glass. Ionic carboxylates of calcium, strontium and aluminum are mainly formed during the setting process. In the present invention, the polymerizable matrix of the light-curable dental ionomer cement contains said one or more polymerizable compounds each having at least one ethylenically unsaturated bond in addition to the polycarboxylic acid, and the 1,3-dipolar compound of the invention.

For dental ionomer cements, the fillers are or contain particulate reactive fillers. A "particulate reactive filler" is a powdered metal oxide or hydroxide, mineral silicate, or ion leachable glass or ceramic, that is capable of reacting with an ionomer in the presence of water to form a hydrogel. Examples of particulate reactive filler materials include materials commonly known in the art of glass-ionomer cements such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass, as well as glasses comprising other elements such as zinc, lanthanum, silver, copper and iron. Suitable particulate reactive fillers further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835.

The particulate reactive filler usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus. The particulate reactive filler may be a multimodal particulate reactive filler representing a mixture of two or more particulate fractions having different average particle sizes. The particulate reactive filler may also be a mixture of particles of different chemical composition. In particular, it is possible to use a mixture of a particulate reactive material and a particulate non-reactive material.

The light-curable dental ionomer cement typically further contains a suitable co-initiator and an inhibitor as described above. Regarding dental ionomer cements, the disclosure of WO 2006/013111 is incorporated herein by reference in its entirety.

Experimental Part

Measurement of Compressive and Yield Strengths

Metal forms with an internal diameter of 4 mm and a height of 6 mm as described in ISO 9917 section 7.4 were used to prepare the specimens. The paste to be measured was filled into the forms, covered with polyester foil, and pressed with metal plates to extrude excess material. The material was then cured for 40 seconds from each end using a dental curing lamp (Spectrum Lite, Dentsply) with an output between 600 and 700 mW/cm$^2$. The forms complete with specimen were drawn across silicon carbide paper (600 grit) until a smooth surface level with the end of the form was obtained, and then the cured specimens were removed from the form. The specimens were stored in water at 37° C. for 24 hours before being tested in a universal testing machine (Zwick) with a crosshead speed of 1 mm/minute. Compressive strength was measured by loading the specimens to failure, and recording the maximum force reached divided by the cross section area of the specimen. The stress strain curve for each specimen was inspected and found to consist essentially of an initial straight portion followed by a curved portion leading to the final breaking point. The straight portion of the curve corresponds to elastic behaviour of the material, whereas the curved portion corresponds to plastic flow. The force at which the stress strain curve first deviated from a straight line was taken as the yield point. The yield point is expressed in MPa, and is calculated by dividing the yield force in Newtons by the cross-sectional area of the specimen. The average value of at least five specimens for each material was calculated.

Measurement of Flexural Strength

Glass tubes with internal diameter 4 mm and length about 30 mm where filled with the composite material to a length of about 25 mm. The tubes were placed in a LiCu Lite light oven (Dentsply) and hardened by exposure to the light for two minutes. After this the resulting hardened composite cylinders were pushed from the tubes and stored in water at 37° C. for 24 hours. The flexural strength was measured by testing the specimens to failure in three-point bending mode using a Zwick universal testing machine. The average value of at least five specimens for each material was calculated.

Lifetime and Depth of Cure

The lifetime (sensitivity to ambient light) of the materials was measured at 10000 lux using the method given in ISO 4049:2000. Note however that ISO 4049 specifies a lower light intensity of 8000±1000 lux. The depth of cure of the materials was also measured according to the method given in ISO 4049:2000.

1. Synthesis of N-nitrosophenylglycine

The precursor N-nitrosophenylglycine was prepared according to the method described in Organic Syntheses, Coll. Vol. 5, p. 962 (1973); Vol. 45, p. 96 (1965). N-phenyl glycine (50 g) was dissolved in water (600 ml) with stirring, and the solution was cooled to below 0° C. in a salt/ice bath mixture. To this was slowly added a cooled solution of sodium nitrite (25 g) in water (150 ml) so that the temperature of the mixture never rose above 0° C. After addition was complete, the mixture was stirred below 0° C. for 40 minutes after which a red-brown solution was obtained with a small amount of brown solid residue. The residue was removed by filtering the solution under vacuum, and the clear liquid was decolorised by treating with charcoal (5 g) for 5 minutes. After filtering off the charcoal, the solution was cooled again and acidified with concentrated hydrochloric acid (50 ml), whereupon a slightly reddish-brown precipitate formed. The mixture was stirred for 10 minutes and then the precipitate was filtered off. This was allowed to dry in air to give a tan coloured powder (48 g).

2. Synthesis of N-phenyl Sydnone

N-phenyl sydnone was prepared by dehydration of the above prepared N-nitrosophenylglycine with acetic anhydride, using the method described in Organic Syntheses, Coll. Vol. 5, p. 962 (1973); Vol. 45, p. 96 (1965).
N-nitrosophenylglycine (48 g) was dissolved in glacial acetic acid (250 ml) in a flask fitted with a drying tube. The mixture was heated with stirring to 100° C. and held for 1½ hours at this temperature. After cooling, the mixture was poured into water (2 liters) and stirred for 15 minutes. The precipitate was filtered, resuspended in ice cold water, and filtered off again. Finally, the precipitate was sucked dry on a vacuum filter to give a cream coloured solid (33 g), mp 133.5-134.5.

Key to Abbreviations
  UDMA Urethane dimethacrylate
  HPGM the reaction product of Hydroxypropyl methacrylate and glutaric anhydride
  EBA Ethoxylated bisphenol A dimethacrylate
  CQ Camphorquinone
  DMABE Dimethylamino benzoic acid, ethyl ester
  BHT butylated hydroxytoluene

EXAMPLES 1 AND 2

Preparation of experimental resin mixtures: Resin mixtures were prepared with initiator and co-initiator concentrations as given in Table 1 by first mixing together UDMA (5 parts), HPGM (5 parts), TMPTMA (5 parts), and EBA (85 parts). The initiators, inhibitors and the 1,3-dipolar compoundswere then added as required in the amounts shown in the table, and dissolved by stirring at 40-50° C. until no solid particles remained.

In the examples shown, camphor quinone was used as photoinitiator, since the 1,3-dipolar compounds used absorb at wavelengths less than 400 nm. The possibility of using a 1,3-dipolar compound that has a significant absorption at wavelengths longer than 400 nm and is capable of acting as a photoinitiator is however not excluded.

Preparation of dental composites: The chosen resin mixture (33.0 g), Aerosil R972 (0.75 g), and silanated glass with a mean particle size of about 0.8 μm (116.25 g) were kneaded together at 40° C. in a vertical kneader for 160 minutes, and the resulting paste was then degassed by stirring for ten minutes at a pressure of 210±10 mbar. Physical properties of the cured pastes were measured as described above and are shown in Table 2.

TABLE 1

Table of resin mixtures comprising 1,3-dipolar compounds

|  | comparative example 1 | resin mix of example 1 | resin mix of example 2 | resin mix of example 3 |
|---|---|---|---|---|
| UDMA parts | 5.0 | 5.0 | 5.0 | 5.0 |
| EBA parts | 85.0 | 85.0 | 85.0 | 85.0 |
| HPGM parts | 5.0 | 5.0 | 5.0 | 5.0 |
| TMPTMA parts | 5.0 | 5.0 | 5.0 | 5.0 |
| camphor quinone | 0.31 | 0.31 | 0.31 | 0.31 |
| dimethylaminobenzoic acid, ethyl ester | 0.6 | 0.6 | 0.6 | 0.6 |
| N-phenylsydnone | — | 0.1 | 0.3 | — |
| BHT | 0.3 | 0.3 | 0.3 | 0.3 |
| N-t-butyl-α-phenyl-nitrone | — | — | — | 0.3 |

TABLE 2

Results for formulations comprising 1,3-dipolar compounds

|  | comparative example 1 | example 1 | example 2 | example 3 |
|---|---|---|---|---|
| Comp. str. MPa | 264.8 | 270 | 278 | 309 |
| Yield str. MPa | 144.9 | 145 | 126 | 133 |
| Flexural str. MPa | 100.7 | 103 | 140 | 136 |
| Lifetime at 10000 lux sec. | 70 | 180 | 250 | 160 |
| Depth of cure mm | 3.6 | 3.6 | 1.8 | 2.7 |

It is seen from the results in Table 2 that the use of a 1,3-dipolar compound in the formulations surprisingly leads to a greatly prolonged lifetime under the influence of ambient light at 10000 lux without any loss of compressive or flexural strength.

The content (including description and claims) of European patent application 08008693.7 filed on May 8, 2008, the priority of which is claimed, is included herein by reference in its entirety.

The invention claimed is:

1. A light-curable dental material comprising
(i) a polymerizable compound having at least one ethylenically unsaturated bond;
(ii) a photopolymerization initiator for polymerizing said polymerizable compound, and
(iii) a 1,3-dipolar compound selected from a group consisting of:
(a) a nitrone of the following formula (VIII):

$$R^6-\underset{R^7}{\overset{R^8}{C}}=\overset{\oplus}{N}-O^{\ominus} \quad (VIII)$$

wherein
$R^6$, $R^7$ and $R^8$ are independently hydrogen; or a substituted or unsubstituted aryl group, arylalkyl group, alkyl group, alkenyl group, alkynyl group, cycloalkyl group or cycloalkylalkyl group; or $R^7$ and $R^8$ form a 5-membered, 6-membered or 7-membered nitrogen-containing ring together with atoms to which they are attached to,
(b) an azide of the following formula (IV):

$$R^1-N=\overset{\oplus}{N}=\overset{\ominus}{N} \quad (IV)$$

wherein $R^1$ of formula (IV) is a substituted or unsubstituted aryl group, arylalkyl group, alkyl group, alkenyl group, alkynyl group, cycloalkyl group or cycloalkylalkyl group,
(c) a diazo compound of the following formula (V):

$$R^1-\underset{}{\overset{R^2}{C}}=\overset{\oplus}{N}=\overset{\ominus}{N} \quad (V)$$

wherein $R^1$ and $R^2$ of formula (V) are independently hydrogen; or a substituted or unsubstituted aryl group, arylalkyl group, alkyl group, alkenyl group, alkynyl group, cycloalkyl group, cycloalkylalkyl group or benzoyl group, or
(d) a nitrilylide of the following formula (VI):

$$R^1-\overset{\oplus}{C}=N-\overset{\ominus}{C}\overset{R^2}{\underset{R^3}{\diagdown}} \quad (VI)$$

wherein $R^1$, $R^2$, and $R^3$ of formula (VI) are independently hydrogen; or a substituted or unsubstituted aryl group, arylalkyl group, alkyl group, alkenyl group, alkynyl group, cycloalkyl group or cycloalkylalkyl group, preferably one of $R^1$, $R^2$, and $R^3$ is not hydrogen.

2. The light-curable dental material according to claim 1, wherein each of the substituted aryl groups, arylalkyl groups, alkyl groups, alkenyl groups, alkynyl groups, cycloalkyl groups or cycloalkylalkyl groups has 1 to 5 substituents that are independently selected from $C_{1-6}$-alkyl, $C_{1-6}$-alkoxy, hydroxy, halo, cyano, nitro, nitroso, mercapto, carboxyl, sulfonate, thiol, amino, trifluoromethyl and polyoxyalkylene groups.

3. The light-curable dental material according to claim 1, wherein said photopolymerization initiator is an α,β-diketone.

4. The light-curable dental material according to claim 1, further comprising a solid particulate filler.

5. The light-curable dental material according to claim 1, wherein the content of said 1,3-dipolar compound based on the total weight of all polymerizable compounds in the dental material is from 0.01 to 2.0 weight-%.

6. The light-curable dental material according to claim 1, wherein the light-curable dental material is selected from the group consisting of a dental composite, dental ionomer cement, dental sealant, dental adhesive, dental adhesion promoter, dental adhesion preventer, dental cement, dental crown-forming material, and dental impression material.

7. Light-cured dental material obtained or obtainable by light curing the light-curable dental material of claim 1.

8. A light-curable surface coating, light-curable ink, or light-curable adhesive material comprising a polymerizable compound having at least one ethylenically unsaturated bond and a 1,3-dipolar compound as a polymerization inhibitor, wherein the 1,3-dipolar compound is selected from a group consisting of:
(a) a nitrone of the following formula (VIII):

$$R^6-\underset{R^7}{\overset{R^8}{C}}=\overset{\oplus}{N}-O^{\ominus} \quad (VIII)$$

wherein
$R^6$, $R^7$ and $R^8$ are independently or a substituted or unsubstituted aryl group, arylalkyl group, alkyl group, alkenyl group, alkynyl group, cycloalkyl group or cycloalkylalkyl group; or $R^7$ and $R^8$ form a 5-membered, 6-membered or 7-membered nitrogen-containing ring together with atoms to which they are attached to,
(b) an azide of the following formula (IV):

$$R^1-N=\overset{\oplus}{N}=\overset{\ominus}{N} \quad (IV)$$

wherein $R^1$ of formula (IV) is a substituted or unsubstituted aryl group, arylalkyl group, alkyl group, alkenyl group, alkynyl group, cycloalkyl group or cycloalkylalkyl group, (c) a diazo compound of the following formula (V):

(V)

wherein $R^1$ and $R^2$ of formula (V) are independently hydrogen; or a substituted or unsubstituted aryl group, arylalkyl group, alkyl group, alkenyl group, alkynyl group, cycloalkyl group, cycloalkylalkyl group or benzoyl group, or (d) a nitrilylide of the following formula (VI):

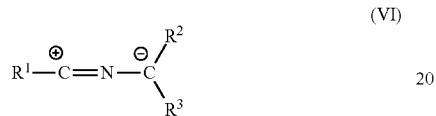

(VI)

wherein $R^1$, $R^2$ and $R^3$ of formula VI are independently hydrogen; or a substituted or unsubstituted aryl group, arylalkyl group, alkyl group, alkenyl group, alkynyl group, cycloalkyl group or cycloalkylalkyl group, preferably one of $R^1$, $R^2$, and $R^3$ is not hydrogen.

* * * * *